(12) United States Patent
Raffay et al.

(10) Patent No.: US 11,389,430 B2
(45) Date of Patent: *Jul. 19, 2022

(54) METHODS OF TREATING RESPIRATORY DISORDERS

(71) Applicant: CASE WESTERN RESERVE UNIVERSITY, Cleveland, OH (US)

(72) Inventors: Thomas M. Raffay, Cleveland, OH (US); Benjamin M. Gaston, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/748,588

(22) Filed: Jan. 21, 2020

(65) Prior Publication Data
US 2020/0206195 A1 Jul. 2, 2020

Related U.S. Application Data

(62) Division of application No. 15/418,126, filed on Jan. 27, 2017, now Pat. No. 10,537,557.

(60) Provisional application No. 62/287,515, filed on Jan. 27, 2016.

(51) Int. Cl.
A61K 31/4178 (2006.01)
A61K 9/00 (2006.01)

(52) U.S. Cl.
CPC ........ A61K 31/4178 (2013.01); A61K 9/0019 (2013.01); A61K 9/0078 (2013.01)

(58) Field of Classification Search
CPC .................................................. A61K 31/4178
See application file for complete search history.

(56) References Cited

U.S. PATENT DOCUMENTS 4,211,239 A 7/1980 Gehmlich et al.
8,691,816 B2 4/2014 Wasley et al.

Primary Examiner — Yong S. Chong
(74) Attorney, Agent, or Firm — Tarolli, Sundheim, Covell & Tummino LLP

(57) ABSTRACT

A method of treating a hyperoxia induced disease or disorder associated with GSNO deficiency in a subject in need thereof includes administering to the subject a therapeutically effective amount of GSNO or a GSNO promoting agent.

11 Claims, 6 Drawing Sheets

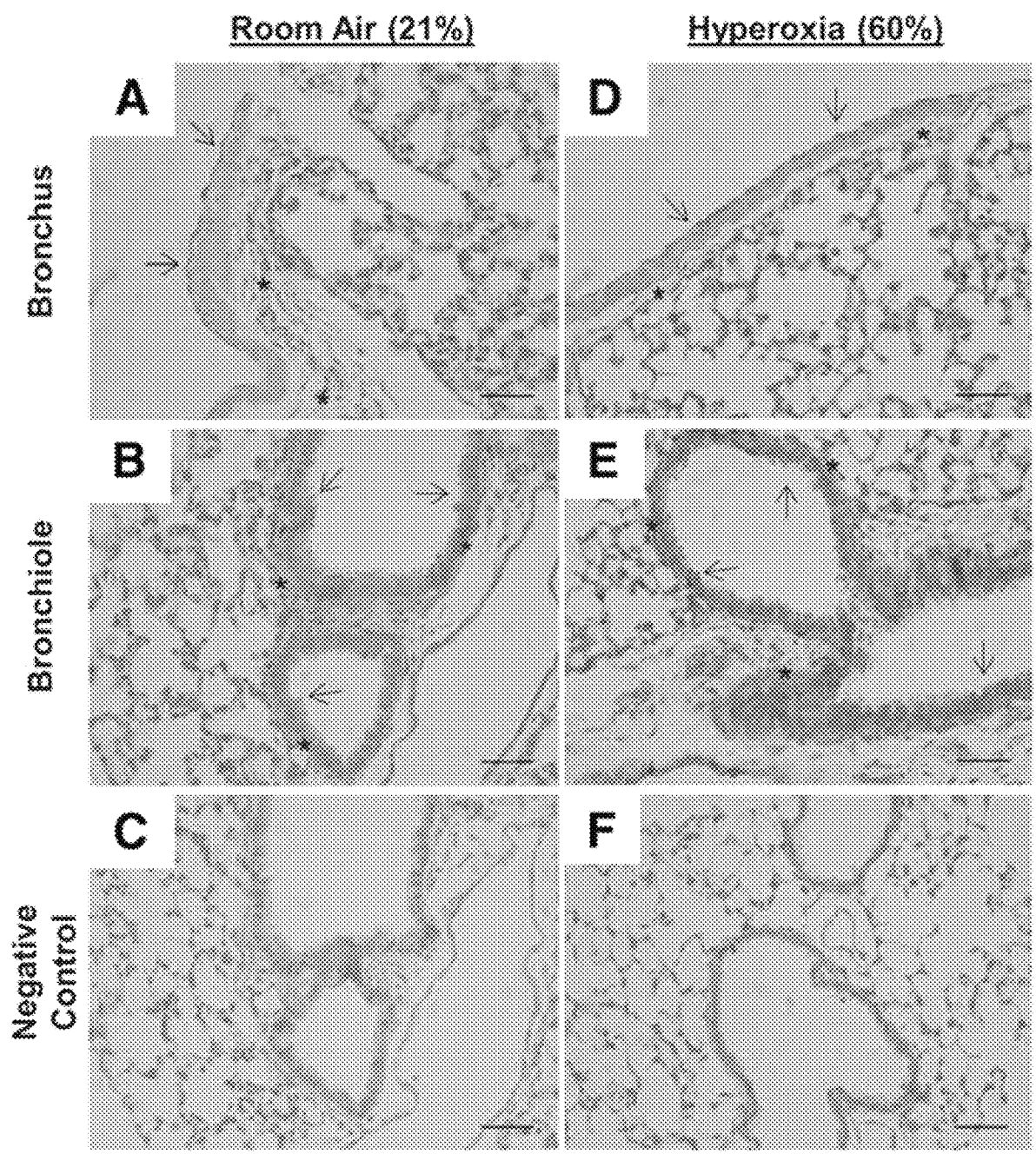
Figs. 2A-F

METHODS OF TREATING RESPIRATORY DISORDERS

RELATED APPLICATION

This application claims priority from U.S. Provisional Application No. 62/287,515, filed Jan. 27, 2016, the subject matter of which is incorporated herein by reference in its entirety.

GOVERNMENT FUNDING

This invention was made with government support under Grant No. K12HD057581-05 and 1P01HL101871 awarded by The National Institutes of Health. The United States government has certain rights in the invention.

TECHNICAL FIELD

This application relates to compositions and methods of modulating S-nitrosoglutathione (GSNO) in subjects with respiratory disorders associated with hyperoxia and particularly relates to the use of GSNO reductase inhibitors to treat hyperoxia-induced air responsiveness, respiratory distress syndrome, and bronchopulmonary dysplasia.

BACKGROUND

Globally, more than 11% of babies are born before 37 weeks of gestation (premature), and the number of premature births is increasing worldwide (Blencowe et al., (2012) *Lancet* 379:2162-2172). Bronchopulmonary dysplasia (BPD) is the major pulmonary morbidity of extreme prematurity, with an estimated 14,000 new diagnoses made each year in the United States (Van Marter (2009) *Semin Fetal Neonatal Med* 14:358-366) and annual care costs upwards of $26 billion (Cole et al., (2011) Pediatrics 127: 363-369). Equally important is the concept that prematurity and BPD may be a chronic respiratory condition. After their initial care, half of premature patients will be rehospitalized for respiratory causes in early childhood (Furman et al., (1996) *The Journal of Pediatrics* 128:447-452). Follow up studies of children and young adults born prematurely show evidence of impaired pulmonary function, manifesting signs of obstructive pulmonary disease with decreased predicted forced expiratory volume in 1 second (FEV1) (Fawke et al. (2010) *Am J Respir Crit Care Med* 182:237-247), decreased predicted forced expiratory flow (FEF25-75%) (Vollsaeter et al. (2013) *Thorax* 68:767-776), and reduced exercise capacity (Vrijlandt et al., (2006) *Am J Respir Crit Care Med* 173:890-896). Indeed, increased airway reactivity and asthma-like symptoms are common long-term pulmonary consequences of both premature birth and BPD (Baraldi et al., (2009) *Early Human Development* 85:S1-3).

S-nitrosothiols (SNOs) are ubiquitous protein molecules in which nitric oxide is bound to a cysteine thiol, which regulate the biologic activity of many target proteins (Foster et al., (2009) *Trends in Molecular Medicine* 15:391-404). One such SNO is S-nitrosoglutathione (GSNO), an endogenous bronchodilator, which exhibits 100-fold more potency than the asthma medication theophylline (Gaston et al., (1994) *J Pharmacol Exp Ther* 268:978-984). GSNO is a critical modulator of airway reactivity in asthmatic animal models (Blonder et al., (2014) *BMC Pulm Med* 14:3). Airway levels of GSNO are dramatically decreased in pediatric cases of severe asthmatic respiratory failure (Gaston et al., (1998) *Lancet* 351:1317-1319) and GSNO reductase (GSNOR, also known as alcohol dehydrogenase 5, adh5), the enzyme responsible for the catabolic breakdown of GSNO, is elevated in asthma patients that display increased airway reactivity (Que et al. (2009) *American Journal of Respiratory and Critical Care Medicine* 180:226-231).

Traditional asthma therapies are not always effective in this patient population. Interestingly, the asthma phenotype in premature infants differs from the allergic asthma seen in their term-born peers (Filippone et al., (2013) *Eur Respir J* 42:1430-1431). The increased risk for airway reactivity in surviving premature neonates is strongly associated with a history of prolonged supplemental oxygen exposure and bronchopulmonary dysplasia (BPD), compared to the reactivity observed in full term peers, which instead is associated with a history of genetic inheritance, allergy, airway inflammation, and cigarette exposures (Halvorsen et al., (2005) *Pediatr Allergy Immunol* 16:487-494). Yet, former premature infants are twice as likely to be prescribed asthma medications compared to their full term school-age classmates (Hack et al., (2005) *JAMA* 294:318-325) and premature infants, with or without BPD, continue to be at very high risk for airway reactivity in infancy and childhood (Fawke et al. (2010) *Am J Respir Crit Care Med* 182:237-247; Been et al., (2014) *PLoS Med* 11:e1001596; Hennessy et al., (2013) *J Pediatr* 163:61-66 e61). Thus, novel therapies are needed in this growing patient population.

SUMMARY

Embodiments described herein relate to the targeted replacement of depleted S-nitrosoglutathione (GSNO) stores in the developing lungs of infant and child subjects born prematurely and potentially treated with prolonged supplemental oxygen by administration of GSNO directly to the subject and/or inhibition of S-nitrosoglutathione reductase (GSNOR) in the subject, and particularly relates to methods of treating and/or preventing hyperoxia induced respiratory disorders, such as respiratory distress syndrome or bronchopulmonary dysplasia (BPD), in premature subjects in need thereof, including those premature subjects receiving life saving newborn interventions, such as supplemental oxygen and mechanical ventilation, by administering to the subjects GSNO and/or a GSNO promoting agent.

In some embodiments GSNO or a GSNO promoting agent can be administered to a subject, such as a premature subject, to raise the subject's GSNO levels and treat disorders associated with GSNO deficiency, such as hyperoxia induced respiratory disorders associated with prolonged supplemental oxygen treatment. The GSNO and/or GSNO promoting agent can be administered to the subject at a therapeutically effective amount(s) in a pharmaceutical composition comprising GSNO and/or a GSNO promoting agent and at least one pharmaceutically acceptable carrier.

Other embodiments described herein relate to methods of treating BPD in a subject in need thereof. Such a method comprises administering a therapeutically effective amount of a pharmaceutical composition including GSNO and/or a GSNO promoting agent and at least one pharmaceutically acceptable carrier.

Still other embodiments described herein relate to methods of treating a BPD, such as hyperoxia induce BPD, in a subject in need thereof by administering a therapeutically effective amount of a pharmaceutical composition comprising a pyrrole inhibitor of GSNOR and at least one pharmaceutically acceptable carrier.

BRIEF DESCRIPTION OF THE DRAWINGS

FIGS. 2(A-F) illustrate GSNOR immunostaining following hyperoxia in lungs of 3-weekold mice. Representative immunohistochemical probe for GSNOR (brown) of inflation-fixed lung sections showed prominent staining of airway epithelium (arrows) and smooth muscle (*) in the bronchus (A, D) and bronchioles (B, E) of both groups. Sections were counterstained with methylene blue. Primary antibody was omitted as a negative control (C, F). Scale bar=50 mm.

DETAILED DESCRIPTION

Figure 1A:
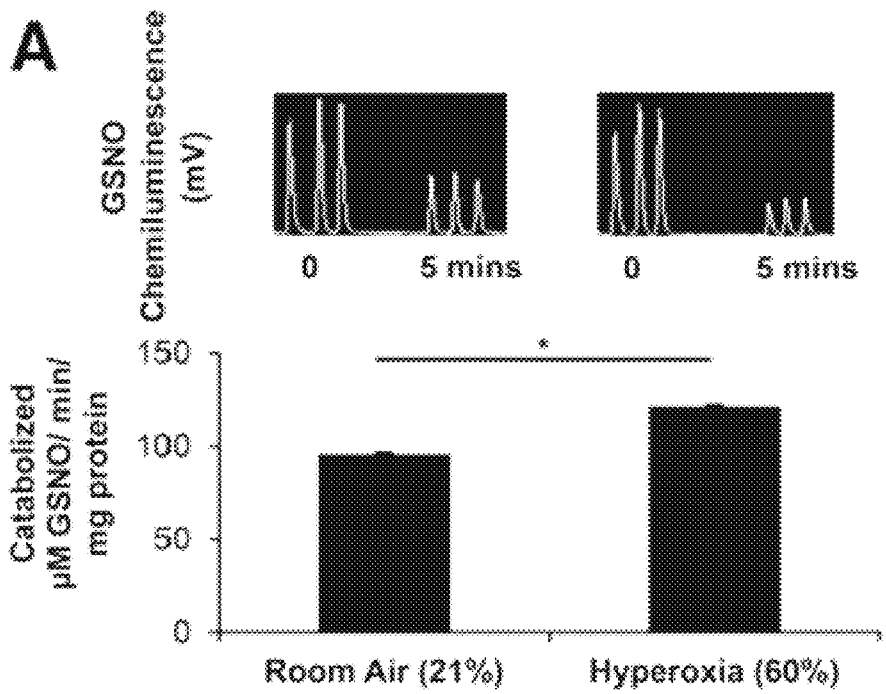
FIGS. 1(A-D) illustrate graphs, plots, and western blots showing an increased GSNOR activity and expression in 3-week-old mice after neonatal hyperoxia exposure. (A) GSNOR activity was assessed by timed GSNO catabolism in lung homogenates, normalized to protein. GSNOR activity was increased in hyperoxia. Representative nitric oxide analyzer tracings in triplicate are shown. Data were normally distributed with equal variance, so a two-tailed Student t test was used. n=5. *P, 0.05. (B) GSNOR kinetics were estimated by generating a Lineweaver-Burke plot at differing GSNO substrate loads. Maximum velocity/Michaelis-Menton constant did not differ between groups. Data were normally distributed with equal variance, so a two-tailed Student t test was used. n=5. (C) Representative Western blot bands from the same gel are shown. Relative expression of GSNOR:b-actin ratio was increased in hyperoxia. Data were normally distributed with unequal variance, so a two-tailed Welch's t test was used. n=12. *P, 0.05. (D) Representative Western blot bands from the same gel are shown. Relative expression of eNOS:b-actin was increased in hyperoxia. Data were normally distributed with equal variance, so a two-tailed Student t test was used. n=4. *P, 0.05.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

The terms "prevent," "preventing," or "prevention" are art-recognized and include precluding, delaying, averting, obviating, forestalling; stopping, or hindering the onset, incidence, severity, or recurrence of a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. In another aspect, the subject is a prematurely born mammal treated with prolonged supplemental oxygen. A patient refers to a subject afflicted with a disease or disorder.

The terms "prophylactic" or "therapeutic" treatment is art-recognized and includes administration to the host of one or more of the therapeutic compositions described herein. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, aryloxycarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO−), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—O$N^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to the targeted replacement of depleted S-nitrosoglutathione (GSNO) stores in the developing lungs of infant and child subjects born prematurely, and potentially treated with prolonged supplemental oxygen, by administration of GSNO directly to the subject and/or inhibition of S-nitrosoglutathione reductase (GSNOR) in the subject. The lungs of premature infant subjects are underdeveloped, and these infant subjects often need assistance with their breathing and oxygen supplementation. Yet, these life-saving interventions, such as supplemental oxygen and mechanical ventilation, may increase these infant's risk for future breathing problems, the most severe of which is bronchopulmonary dysplasia (BDP).

Utilizing a hyperoxic neonatal mouse model of BPD, it was found that subjects raised in hyperoxia had increased activity and protein expression of the primary catabolic enzyme of S-nitrosoglutathione reductase (GSNOR). It was also found that GSNO supplementation and/or inhibition of GSNOR has protective effects on airway hyperreactivity found after neonatal oxygen exposure in a mouse model of BPD.

Without being bound by theory, it is believed that an increase in the expression and catabolic activity of GSNOR, the enzyme responsible for reducing and inactivating GSNO, through altered post-transcriptional regulation by microRNA-342-3p results in neonatal subjects developing pulmonary toxicities and/or respiratory disorders when treated with prolonged supplemental oxygen. Therefore, it is contemplated that targeted direct replacement of depleted GSNO stores in the developing lung of subjects exposed to hyperoxia or inhibition of the catabolic activity of GSNO can be therapeutically effective in the treatment of infant and child subjects born prematurely and that have been treated with prolonged supplemental oxygen.

In some embodiments, a method of treating and/or preventing hyperoxia induced respiratory disorders, such as respiratory distress syndrome or bronchopulmonary dysplasia (BPD), in premature subjects in need thereof, such as a premature or prenatal subject exposed to supplemental oxygen treatment, can include administering to the subject a therapeutically effective amount of GSNO or a GSNO promoting agent.

In some embodiments, GSNO used in the methods described herein can include aerolized GSNO this is provided in a pharmaceutical composition, which is administered to the subject via inhalation. For example, GSNO can be provided in an aerolized pharmaceutical composition at a concentration of about 1 µM to about 100 mM GSNO (e.g., about 10 mM GSNO) with a pharmaceutically acceptable carrier that is administered to the subject via inhalation.

The GSNO promoting agent for use in the methods described herein can include any agent capable of increasing the expression of GSNO and/or inhibiting the catabolic activity of GSNOR in a subject. Examples of GSNO promoting agents for use in the methods described herein include ADH inhibitors, such as GSNOR inhibitors, AKR inhibitors, and SNO-CoAR inhibitors. Administration of ADH inhibitors, AKR inhibitors, and/or SNO-CoAR inhibitors as well as SNO-CoA (or derivatives thereof e.g., SNO-cysteamine) to a subject in need thereof can raise GSNO levels in the subject and treat diseases or disorders associated with GSNO deficiency, such as BPD, and hyperoxia induced airway hyperresponsiveness.

In some embodiments, the GSNO promoting agent can be a GSNOR inhibitor (also known as an ADH5 inhibitor). In one example, the GSNOR inhibitor can include a pyrrole inhibitor of GSNOR. In some embodiments, the pyrrole inhibitor of GSNOR can be a compound having the following formula:

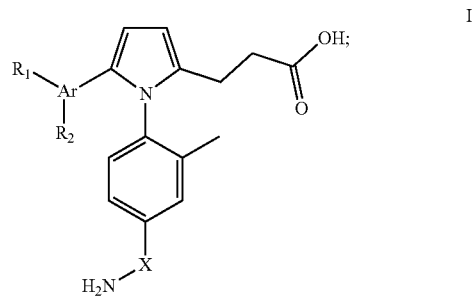

wherein Ar is an aryl, such as a phenyl and thiophenyl;
$R_1$ is selected from the group consisting of unsubstituted or substituted imidazolyl, chloro, bromo, fluoro, hydroxy, and methoxy;
$R_2$ is selected from the group consisting of hydrogen, methyl, chloro, fluoro, hydroxy, methoxy, ethoxy, propoxy, carbamoyl, dimethylamino, amino, formamido, and trifluoromethyl; and
X is selected from the group consisting of CO and $SO_2$; and pharmaceutically acceptable salts, stereoisomers, prodrug, or metabolites thereof.

One example of an ADH5 inhibitor/GSNOR pyrrole inhibitor is GSNOR pyrrole inhibitor N6022, which is commercially available from Nivalis Therapeutics, Boulder, Colo. N6022 has the following formula:

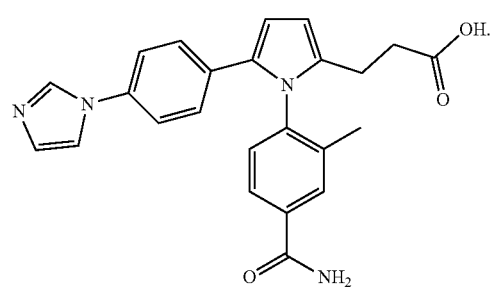 [SMILES: Cc1cc(C(N)=O)ccc1-n1c(CCC(=O)O)ccc1-c1ccc(-n2ccnc2)cc1]

Additional inhibitors of GSNOR for use in methods recited herein are described in U.S. Patent Application Publication Nos: 2011/0136875, 2011/0136881, 2011/0144110, 2011/0144180, 2012/0245210, 2013/0253024, 2014/0057957, 2014/0113938, 2014/0113945, 2014/0155447, 2014/0194425, 2014/0194481 and U.S. Pat. Nos. 8,470,857, 8,642,628, 8,673,961, 8,686,015, 8,691,816, 8,759,548, 8,846,736, 8,957,105, 9,029,402, 9,138,427, and 9,180,119 all of which are incorporated herein by reference in their entirety.

Other ADH inhibitors that can be used as a GSNO promoting agent can include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication US 2003/0138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme.NAD$^+$.inhibitor complex, in which pyrazole nitrogens interact with both zinc and NAD$^+$. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Still other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

In some embodiments, the AKR inhibitor can be a selective AKR1A1 inhibitor or a partially selective AKR1A1 that can inhibit other aldo-keto reductase family members, such as AKR1B1. In some embodiments, the AKR1A1 inhibitor can have an IC$_{50}$≤100 nM. In other embodiments, the AKR1A1 inhibitor can have a selectivity for AKR1A1 versus AKR1B1≥10 times. In other embodiments, the AKR1A1 inhibitor can have a selectivity for AKR1A1 versus other AKRs≥50 times. In still other embodiments, the AKR1A1 inhibitor can have an AKR1A1 IC$_{50}$≤25 nM and an AKR1B1/AKR1A1 IC$_{50}$≤300 nM (e.g., less than 100 nM).

Examples of selective and partially selective AKR1A1 inhibitors can include Imirestat (2,7-Difluoro-2'H,5'H-spiro[fluorene-9,4'-imidazolidine]-2',5'-dione) and analogues thereof.

In some embodiments, the imirestat analogues can include compounds selected from the group consisting of:

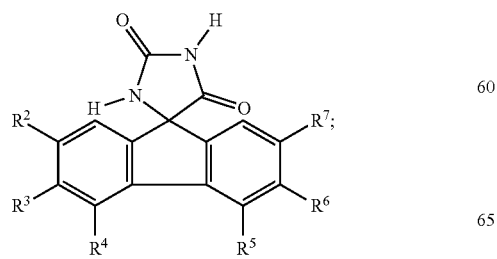

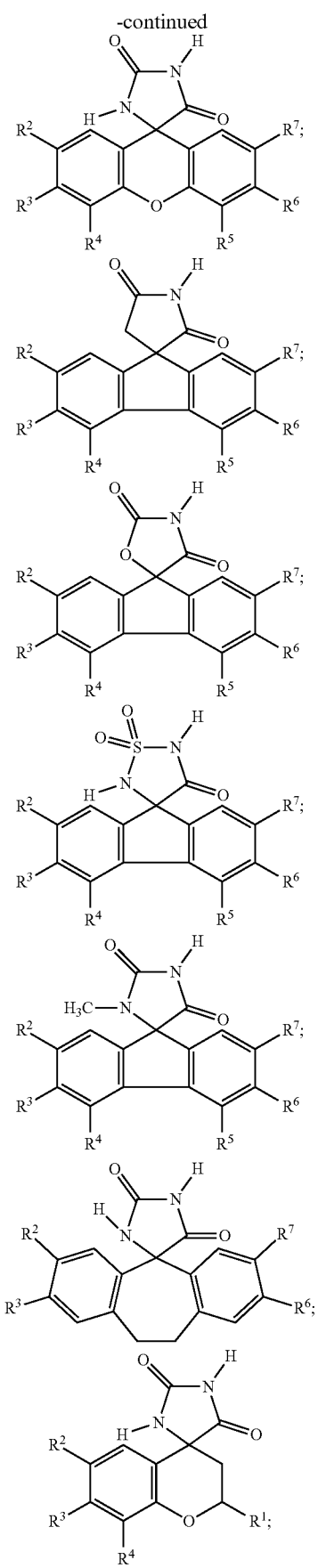

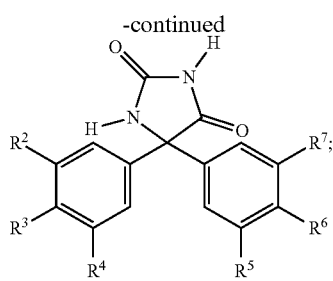

each $R^1$, $R^2$, $R^3$, $R^4$, $R^5$, $R^6$, and $R^7$ are the same or different and are one or more substituent selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof; and pharmaceutically acceptable salts thereof.

Other examples of selective and partially selective AKR1A1 inhibitors can include Methyl[4-oxo-2-(substituted benzoylimino)-3-(substituted phenyl)thiazolidin-5-ylidene]acetate derivatives recited in S. Ali et al., "Design, synthesis and molecular modeling of novel methyl[4-oxo-2-(aroylimino)-3-(substituted phenyl)thiazolidin-5-ylidene] acetates as potent and selective aldose reductase inhibitors", Med. Chem. Commun., 2012, 3, 1428-1434. These AKR1A1 inhibitors can have the following formula:

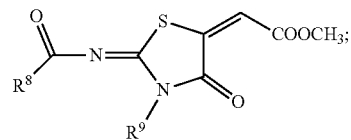

wherein $R^8$ and $R^9$ are independently selected from the group consisting of substituted and unsubstituted aryls.

Other examples of selective and partially selective AKR1A1 inhibitors can include benzothiazolyl substituted iminothiazolidinones and benzamido-oxothiazolidines recited in Saeed et al., "Benzothiazolyl substituted iminothiazolidinones and benzamido-oxothiazolidines as potent and partly selective aldose reductase inhibitors", Med. Chem. Commun., 2014, 5, 1371-1380. These AKR1A1 inhibitors can have the following formula:

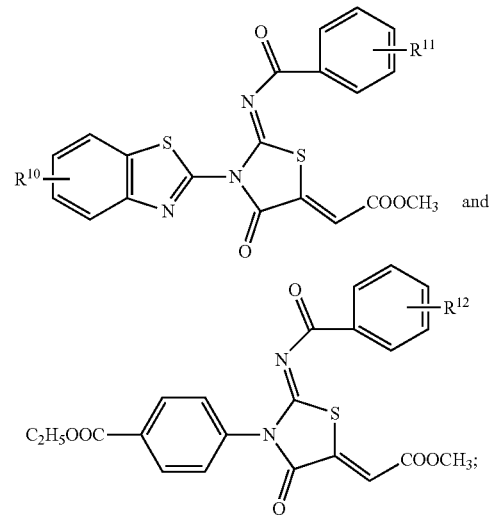

wherein $R^{10}$, $R^{11}$, or $R^{12}$ include one or more substitutent and are each independently selected from the group consisting of H, a halogen (e.g., 6-Br, 3-Cl, 2-F, 2-Br, 5,6-di-Cl, 2,4-di-Cl), lower alkyl, and methoxy (e.g., 4-OCH$_3$, 3,4-OCH$_3$).

Still other examples of selective and partially selective AKR1A1 inhibitor are disclosed in the following publications: Mechanism of Human Aldehyde Reductase: Characterization of the Active Site Pocket, Oleg A. Barski et al., Biochemistry 1995, 34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., ChemMedChem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999.), Inhibition of aldehyde reductases, Philip J. Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

In other embodiments, the GSNO promoting agent can include an agent that reduces or inhibits ADH and/or AKR expression, such as ADH6 expression or AKR1A1 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the ADH and/or AKR expression in a cell. RNAi constructs comprise RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to small interfering RNA (siRNA) molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, Nucleic Acids Res, 25:776-780; J Mol Recog 7:89-98; Nucleic Acids Res 23:2661-2668; Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs siRNAs. These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Proc Natl Acad Sci USA, 98:9742-9747; EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Genes Dev, 2002, 16:948-58; Nature, 2002, 418:38-9; RNA, 2002, 8:842-50; and Proc Natl Acad Sci, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

An RNAi construct for use in a method described herein can include a small non-coding RNA molecule known as microRNA (miRNA) which functions in RNA silencing and post-transcriptional regulation of gene expression. In an exemplary embodiment, miRNA can include miR-342-3p or a miR-342-3p mimic to silence transcription and protein expression of GSNOR in a subject.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the GSNOR in a lung tissue cells of a subject in need thereof. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5α cells. After positive clones are selected, plasmid can be transfected into 293T cells by calcium precipitation. The viral supernatant collected containing shRNA can then be used to infect mammalian cells in order to down regulate the AKR1A1.

AKR1A1 siRNA, shRNA plasmids, and shRNA lentiviral particle gene silencers are commercially available from Santa Cruz Biotechnology under the product names sc-78566, sc-78566-SH, and sc-78566-V.

In another embodiment, the ADH and/or AKR inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., AKR1A1 or GSNOR/ADH5).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Bio search, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In some embodiments, GSNO and/or the GSNO promoting agent can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

Pharmaceutical compositions comprising GSNO and/or the GSNO promoting agent can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc.

Specifically, GSNO and/or the GSNO promoting agent can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For targeted delivery to a subject's airway or lung tissue in accordance with a method described above, an inhalation formulation can be used to achieve high local concentrations. Formulations suitable for inhalation include dry powder or aerosolized or vaporized solutions, dispersions, or suspensions capable of being dispensed by an inhaler or nebulizer into the endobronchial or nasal cavity of a subject in need thereof. In some embodiments, GSNO and/or the GSNO promoting agent can be delivered yea aerosol spray from pressured container or dispenser that contains a suitable propellant, e.g., a gas such as carbon dioxide, a nebulized liquid, or a dry powder from a suitable device.

By way of example, an aerosol of 10 mM GSNO, at a dose of 0.05 ml/kg, can be delivered to the subject's airway on a daily basis. Additional embodiments include 1) the use of a similar concentration by dry powdered inhaler, and 2) delivery of greater concentrations to the lower respiratory tract by an aerosol bronchoscopy, 3) by atomizer to the nasal mucosa and osteomeatal complex, 4) to the eustachian tube. This dosing has as its objective restoring or increasing normal levels of GSNO to the airway of a subject in need thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In some embodiments, GSNO and/or a GSNO promoting agent can be prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions that include GSNO and/or a GSNO promoting agent can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, silicified microcrystalline cellulose, gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crosspovidone, sodium starch glycolate, and mixtures thereof; (4) lubricants, including agents that act on the flowability of a powder to be compressed, include magnesium stearate, colloidal silicon dioxide, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose; lactose such as lactose monohydrate, and lactose anhydrous; dibasic calcium phosphate, mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In some embodiments, pharmaceutical compositions comprising GSNO and/or a GSNO promoting agent can be used for prophylactic therapy. For example, a therapeutically effective amount of GSNO and/or a GSNO promoting agent can be administered to a premature subject in need thereof prior to oxygen exposure or during daily oxygen exposure to prevent the subject from developing BPD.

In certain embodiments, subjects can include neonatal human patients experiencing treatment with prolonged supplemental oxygen. Neonatal patients commonly develop wheezing disorders and bronchopulmonary dysplasia BPD following such prolonged targeted oxygen supplementation treatment necessary for neonatal survival.

While premature infants with BPD have the most severe lung disease, it is further contemplated that all premature infants, even those thought to be late-preterm or near term, are at significantly increased risk for wheezing and asthma than their full-term peers. Therefore, in certain embodiments, subjects administered therapeutic GSNO repleting compositions in accordance with a method described herein can further include premature infants without BPD who can benefit from GSNOR inhibition.

In general, the dosage, i.e., the therapeutically effective amount, ranges from 1 µg/kg to 10 g/kg body weight and often ranges from 10 µg/kg to 1 g/kg or 10 µg/kg to 100 mg/kg body weight of the subject being treated, per day. In a particular embodiment, the therapeutically effective amount of the GSNOR inhibitor, N6022, ranges from 1 mg/kg to 100 mg/kg body weight daily.

In some embodiments, the therapeutically effective amount is the amount required to decrease by at least 1%, 5%, 10%, 20%, 30%, 40%, 50%, 60%, 70%, 80%, 90%, or even completely reverse airway hyperreactivity observed in a subject with BPD. In some embodiments, the therapeutically effective amount can be the amount required to increase lung compliance (Crs) at least 1%, 5%, 10%, 20%, 30%, 40%, 50%, 60%, 70%, 80%, 90%, or more and/or decrease lung respiratory resistance (Rrs) associated with hyperoxia in a premature human subject administered supplemental oxygen by at least 1%, 5%, 10%, 20%, 30%, 40%, 50%, 60%, 70%, 80%, 90%, or more. In some embodiments, the therapeutically effective amount can be the amount required to produce a measurable increase (e.g., at least 1%, 5%, 10%, 20%, 30%, 40%, 50%, 60%, 70%, 80%, 90%, or more) in forced expiratory volume in 1 second (FEV1), forced expiratory flow (FEF2) and/or increased exercise capacity in the subject.

In some embodiments, GSNO and/or a GSNO promoting agent can be administered in combination with other NO donors, including SNO-CoA, which is shown to have novel activity in regulating sterol biosynthesis and CoA metabolism. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat.

No. 6,359,182 and in WO 02/34705. Examples of S-nitroso compounds, including S-nitrosothiols useful herein other than GSNO, include, for example, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine), and perfluorocarbons that have been saturated with NO or a hydrophobic NO donor. GSNO and/or GSNO promoting agents can also be combined with R(+) enantiomer of amlodipine, a known NO releaser (Zhang at al., J. Cardiovasc. Pharm. 39: 208-214 (2002)).

In some embodiments, GSNO and/or a GSNO promoting agent can be administered in a combinatorial therapy or combination therapy that includes administration of the GSNO and/or a GSNO promoting agent with one or more additional active agents. The phrase "combinatorial therapy" or "combination therapy" embraces the administration of GSNO and/or a GSNO promoting, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, GSNO and/or GSNO promoting agents can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5α-reductase inhibitors such as finasteride and the compounds described in U.S. Pat. No. 5,516,779, cyproterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473).

Other active compounds, which can be present in pharmaceutical compositions include aminexil and its derivatives, 60-[(9Z,12Z)octadec-9,12-dienoyl]hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

It will also be appreciated that certain selective GSNO promoting agents that inhibit some ADHs, AKRs, and/or SNO-CoARs can be administered in combination with other selective ADH inhibitors, AKR inhibitors, and/or SNO-CoAR inhibitors that inhibit other ADHs, AKRs, and/or SNO-CoARs. For example, a selective GSNOR/ADH5 inhibitor can be administered in combination with an ADH3 inhibitor.

The invention is further illustrated by the following examples, which is not intended to limit the scope of the claims.

Example

In this Example, we show that increased GSNOR activity underlies the perinatal airway hyperreactivity observed in BPD and thus GSNO repletion can treat perinodal airway hyperreactivity and BPD. We show these results in a hyperoxic murine model of BPD and airway hyperreactivity. Murine lung development continues postnatally and is similar to the premature human lung. Hyperoxia exposure in neonatal mice creates a lesion very similar to human BPD with characteristic long-term alveolar and parenchymal remodeling, manifesting increased airway reactivity. We used this model to investigate the role of GSNOR in BPD airway hyperreactivity. We demonstrate that neonatal hyperoxia increases GSNOR expression and activity, in part through a microRNA (miR), and GSNO-based treatments can abolish BPD airway hyperreactivity.

Materials and Methods

Animal Hyperoxic Exposure

Animal protocols were approved by the Institutional Animal Care and Use Committee at Case Western Reserve University (Cleveland, Ohio). Timed pregnant C57BL/6 mice (Charles River Laboratories, Wilmington, Mass.) were maintained on 12-hour light-dark cycles with ad libitum standard food and water. Within 24 hours of birth, litters were pooled and randomized into exposure groups. Paired with a nursing dam, pups were raised in 60% oxygen or room air (21%) for 21 days. Hyperoxia-exposed animals were housed in standard cages placed in a 38-L Plexiglas chamber with a continuous flow of blended oxygen (2 L/min). Oxygen concentrations were monitored twice daily via an oxygen analyzer (miniOX I; MSA Medical, Gurnee, Ill.). To control for oxygen exposures, nursing dams were rotated between paired litters during weekly cage changes. Ventilator studies were conducted and/or tissue harvested within 24 hours of removal from hyperoxia at 3 weeks. A subgroup of animals was returned to room air following 3 weeks of initial hyperoxia exposure and subsequently recovered to 6 weeks of age for adult lung mechanic and GSNOR activity studies.

GSNOR Activity by Copper Cysteine Reagent and Nitric Oxide Analysis

Enzyme activity in lung homogenates from 3-weekold and 6-week-old mice was assessed by timed GSNO catabolism and quantification by copper-cysteine reagent and nitric oxide analysis (2C/NOA). After terminal anesthesia with i.p. ketamine/xylazine (Pfizer, St. Joseph, Mo.; Lloyd Laboratories, Shenandoah, Iowa), lungs from mice were harvested and rinsed in ice-cold phosphate-buffered saline (PBS, pH 7.4), placed in centrifuge tubes, snap-frozen in liquid nitrogen, and stored at 280° C. Tissue in ice-cold radioimmunoprecipitation assay lysis buffer containing protease inhibitors (Santa Cruz Biotechnology, Dallas, Tex.) was homogenized, and protein levels were quantified by Pierce bicinchoninic acid (BCA) protein assay kit (Thermo Scientific, Waltham, Mass.). A known quantity of GSNO (28 mM) was loaded with coreagents (300 mMNADH and 2 mM glutathione; Sigma-Aldrich, St. Louis, Mo.) and equivalent protein quantities of frozen lung homogenates in PBS. After incubation for 5 minutes at 37° C., the reaction was quenched by a 1:10 dilution of ice-cold PBS. Uncatabolized GSNO was then measured by 2C/NOA, as previously described (Rogers et al., 2013). Briefly, samples were injected into a temperature-controlled reservoir containing copper cysteine reagent (pH, 6.9) with a continuous flow of blended helium. Gas-phase nitric oxide was liberated from GSNO contained in the injected samples and detected by ozone-based chemiluminescence using an inline nitric oxide analyzer (Seivers 280i; GE Instruments, Boulder, Colo.). GSNO content was determined by fitting chemiluminescence peaks to a GSNO standard curve and normalizing to sample protein levels. Enzyme kinetics were further derived from a Lineweaver-Burke double-reciprocal plot utilizing a total of three loading doses of GSNO (14, 28, and 56 mM).

Western Blot

Harvested snap-frozen lungs from 3-week-old mice were homogenized in ice-cold radioimmunoprecipitation assay lysis buffer containing protease inhibitors (Santa Cruz Biotechnology), and protein levels were determined by BCA assay (Thermo Scientific). Samples of 50 mg protein were separated by electrophoresis with 4-15% Mini Protean TGX precast gels (Bio-Rad Laboratories, Hercules, Calif.) and transferred to nitrocellulose membranes (P:0 on iBlot; Invitrogen, Rehovot, Israel). Membranes were blocked with 5% milk or bovine serum albumin (BSA; Sigma-Aldrich) and incubated in GSNOR primary antibody (1:1000 in milk; observed band 40 kDa; Proteintech, Rosemont, Ill.), endothelial NOS primary antibody (1:1000 in BSA; observed band 140 kDa; BD Transduction Laboratory, San Jose, Calif.), iNOS primary antibody (1:1000 in BSA; observed band 145 kDa, Abcam, Cambridge, Mass.), or neuronalNOS primary antibody (1:500 in milk; expected band 161 kDa; Abcam) overnight at 4° C. and then horseradish peroxidase-conjugated secondary anti-rabbit antibody (1:3000; Santa Cruz, Dallas, Tex.) or anti-mouse antibody (1:3000; Santa Cruz), as appropriate, for 1 hour at room temperature. As a loading control, membranes were stripped (Pierce Restore; Thermo Scientific) and reprobed with b-actin primary antibody (1:2000 in milk; observed band 42 kDa, Abcam) and anti-mouse horseradish peroxidase-conjugated secondary antibody (1:5000; Abcam). Band intensities were quantified and normalized to b-actin using Super Signal West Pico Chemiluminescent Substrate (Thermo Scientific). Relative intensities were measured using densitometry software (Image J, NIH).

Immunohistochemistry

After terminal anesthesia (ketamine/xylazine), lungs of 3-week-old mice were inflated with intratracheal 10% formalin at 25 cm $H_2O$; tissue was saline perfused with PBS (pH 7.4) and then formalin. The right lung was postfixed in 10% formalin at 4° C. for >24 hours, tissue was paraffin embedded, and 5-mm-cut sections were processed. Tissue sections were immunoblotted with GSNOR primary antibody (1:200; Proteintech) at 4° C. overnight and then biotinylated goat anti-rabbit secondary antibody (1:10,000; Vector Laboratories, Burlingame, Calif.) using Vectastain ABC kit, and next counterstained with methylene blue (Sigma-Aldrich), as previously described (Marozkina et al., 2012). Primary antibody was omitted as a negative control. Airways were similarly imaged (Rolera XR CCD camera; Q Imaging, Surrey, Canada).

miR Microarray

RNA was extracted from saline-perfused snapfrozen lungs of 3-week-old mice preserved in RNAlater-ICE reagent using a miRVana column isolation kit (Life Technologies, Carlsbad, Calif.). RNA was quantified by Nanodrop spectroscopy (Thermo Scientific), and microarray analysis of all mature mouse probes from the miRBase V21 library were compared between groups (LC Sciences, Houston, Tex.). Utilizing a gene-miR interaction search (Dweep et al., 2011, 2014) for the 39 untranslated region binding site of GSNOR mRNA (gene id: adh5, alcohol dehydrogenase 5), the most predicted miR candidates were cross-referenced with the microarray results, and high-probability miRs were selected and confirmed by quantitative reverse-transcription polymerase chain reaction (qRT-PCR).

qRT-PCR

RNA was extracted from frozen lungs of 3-week-old mice using TRIzol reagent (Life Technologies) and quantified by Nanodrop spectroscopy (Thermo Scientific). cDNA was generated from 1 mg RNA by reverse transcription using qScript cDNA synthesis kit (Quanta Biosciences, Gaithersburg, Md.). Real-time quantitative polymerase chain reaction was performed on a StepOne PCR system (Applied Biosystems, Foster City, Calif.) using TaqMan probes (Life Technologies) for GSNOR (Mm00475804_g1) compared with 25% diluted b-actin control (Thermo Scientific) with PerfeCTa qPCR FastMix, UNG, ROX (Quanta Biosciences, Gaithersburg, Md.). For microRNA qRT-PCR, RNA was similarly extracted as in the miR microarray studies. cDNA was generated using TaqMan primerspecific assays and MicroRNA Reverse Transcription kit, and realtime quantitative polymerase chain reaction was performed using TaqMan MicroRNA assays for microRNA-342-3p (2260, Thermo Scientific) compared with snRNA-U6 control (001973, Thermo Scientific) with TaqMan Universal Master Mix, No AmpErase UNG (Life Technologies). Fold changes are reported utilizing $2^{-ddCT}$ method and StepOne software v2.3 (Applied Biosystems).

Transfection with Mmu-miR-342-3p and Cytomix Activation of RAW 264.7 Cells

RAW 264.7 macrophage cells (American Type Culture Collection, Manassas, Va.) were cultured in Gibco Dulbecco's modified Eagle's medium with 10% fetal bovine serum and 1% penicillin-streptomycin (Life Technologies). Cells were transfected with 20 nM miRIDIAN miR mimic for mmu-miR-342-3p or with a miR mimic transfection control, cel-miR-67 (Dharmacon, GE Lifesciences, Lafayette, Colo.) by AMAXA electroporation utilizing Nucleofector Kit V (Lonza Group, Basel, Switzerland), per manufacturer's instructions. After 48 hours, cells were harvested for protein or RNA studies, and pellets were snap frozen. Protein levels were determined by BCA assay, and protein was equivalently loaded for gel electrophoresis and Western blot analysis of GSNOR:b-actin, as described above. RAW 264.7 qRT-PCR for miR-342-3p was similarly performed on transfected cells, as described above, to confirm increased gene expression resulting from transfection. Additionally, untransfected RAW 264.7 cells in culture media were incubated with cytomix (10 ng/mL each interleukin-1b, tumor necrosis factor-a, interferon-g, and lipopolysaccharide; Sigma-Aldrich) or vehicle for 10 hours to measure changes in GSNOR expression in the activated macrophage (Tan et al., 2013).

Synthesis of GSNO

GSNO was synthesized in-house. Briefly, using a nitrogen sparge at 4° C. in light-protective conditions, reduced L-glutathione (2 g) in purged hydrochloric acid (2 N) and purged ultrapure water was S-nitrosylated with sodium nitrite (455 mg) over 30-60 minutes (Sigma-Aldrich). The resulting pink GSNO solution was vacuum filtered, mixed with 10 mL purged 50% acetone for 10-20 minutes, and filtered again. Samples were lyophilized and stored at 280° C. Concentration was confirmed by Saville assay.

GSNOR Inhibitor Administration

N6022 is a selective small molecule reversible inhibitor of GSNOR. Powdered N6022 (Nivalis Therapeutics, Boulder, Colo., purchased through MedChem Express, Monmouth Junction, N.J.) was reconstituted in sterile PBS (pH 7.4) and administered to hyperoxia exposed mice as a single 1 mg/kg i.p. injection the day prior to testing lung mechanics.

Lung Mechanics

Under general anesthesia (i.p. ketamine/xylazine), mice were placed supine on a heated surgical table, tracheostomized, and ventilated via a 19-gauge blunt-tip cannula with a commercial rodent ventilator (flexiVent; SCIREQ, Montreal, Canada). Animals were paralyzed (i.p. pancuronium bromide; Sigma-Aldrich) and ventilated at default settings: tidal volume of 10 mL/kg, a rate of 150 breaths/min, a positive end expiratory pressure of 3 cm $H_2O$, and a $FiO_2$ of 50%. Following two recruitment deep inflations of sustained inspiration up to a pressure of 30 cm $H_2O$ for 3 seconds, 10 mM GSNO or saline vehicle was aerosolized over 10 seconds using an ultrasonic nebulizer (Aeroneb; SCIREQ) diverted into the ventilator's inspiratory flow. Inhaled GSNO concentration was chosen based upon the published studies in ventilated guinea pigs and human trials in cystic fibrosis. After 5 minutes had elapsed, two recruitment deep inflations were again delivered, and increasing methacholine doses of 0, 12.5, 25, 50, 100, and 200 mg/mL were similarly aerosolized over 10 seconds to generate a dose-response curve. Using computer software (flexiWare 5.1, Version 7.2, SCIREQ), five measurements of respiratory system resistance (Rrs) were calculated by a 2.5 Hz single-frequency forced oscillation maneuver (Snapshot 150), and an average was reported for each methacholine dose. Respiratory mechanics were measured in both 3-week-old mice immediately following sustained hyperoxia exposure and separate 6-week-old mice that were recovered in room air following the initial 3 weeks of hyperoxia exposure.

Statistics

Data are expressed as means±S.E.M. A minimum of two litters or experiments was used for each study; n represent individual animals or cell transfections. Data containing two groups were first tested for normality and variance and then analyzed by two sample student t test, Welch's t test, or Mann-Whitney U test, as appropriate. For multiple comparisons, analysis of variance with Tukey-Kramer post hoc test was used. Alterations in airway reactivity with increasing doses of methacholine were compared by two-way analysis of variance repeated-measures analysis with Tukey-Kramer post hoc comparisons using a fixed-sequence method from highest to lowest methacholine dose. P, 0.05 was considered statistically significant.

Materials

If not otherwise stated, all reagents and chemicals were purchased from Sigma-Aldrich and were of an analytical grade.

Results

GSNO Catabolism is Increased after Neonatal Hyperoxia

Figure 1B:
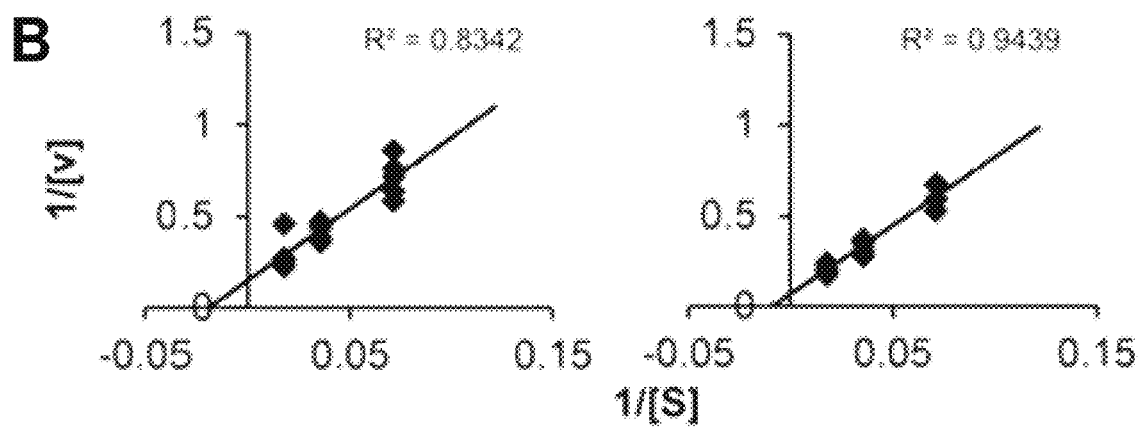

Increased expression of GSNOR causes loss of the endogenous bronchodilator, GSNO, and increased bronchial hyperreactivity. Using 2C/NOA, we have shown that GSNOR activity (NADH-dependent GSNO catabolism/min/mg protein) in the lungs of 3-week-old mice raised in neonatal hyperoxia was higher than that of room air controls (FIG. 1A). The Lineweaver-Burke plots of estimated maximum velocity and Michaelis-Menton constant tended to be increased among the hyperoxia-exposed group (FIG. 1B), yet the ratio of maximum velocity/Michaelis-Menton constant was similar between groups. Although these kinetic findings could indicate loss of a noncompetitive inhibitor, the most likely explanation was increased GSNOR expression in hyperoxia. GSNOR activity was also measured by 2C/NOA in the lung homogenates from 6-week-old mice who were exposed to 3 weeks of hyperoxia and then recovered in room air. GSNOR activity remained significantly increased in the hyperoxia-exposed roomair-recovered mice, compared with 6-week-old room air controls (11.84±0.22 versus 11.08±0.17 mM/min/mg protein, respectively, P, 0.05), albeit with less catabolic activity permgprotein than at 3 weeks of age.

GSNOR Expression is Increased after Neonatal Hyperoxia

Figure 1C:
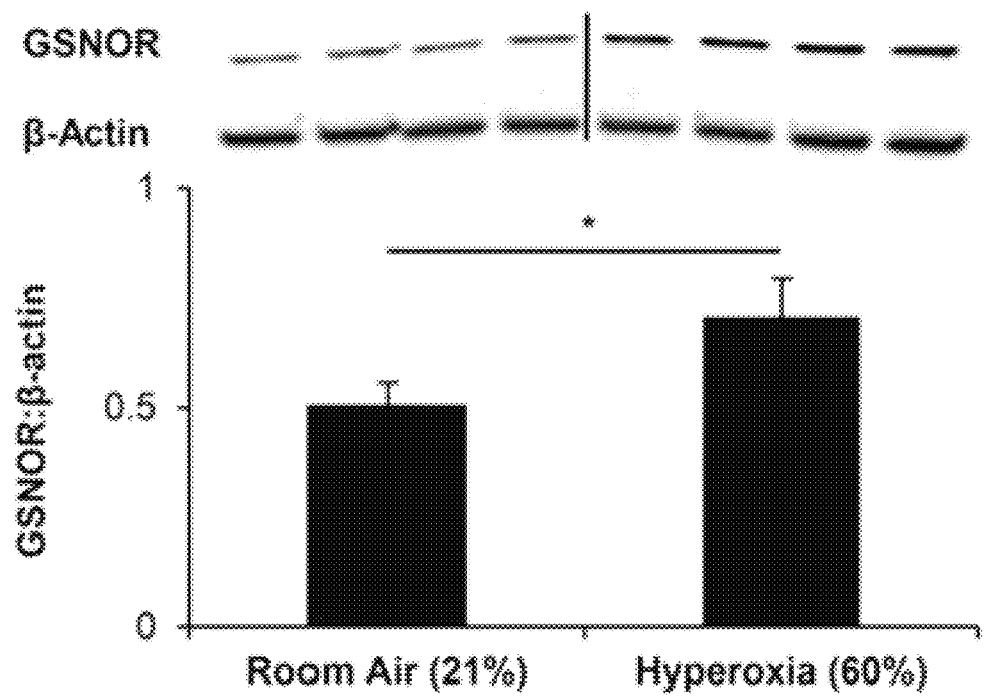

Consistent with the GSNOR kinetic data in 3-week-old mice, the relative protein expression of GSNOR was increased in the lungs of 3-week-old mice raised in hyperoxia when compared with room air controls, as assessed by Western blot (FIG. 1C).

eNOS Expression is Increased after Neonatal Hyperoxia

Figure 1D:
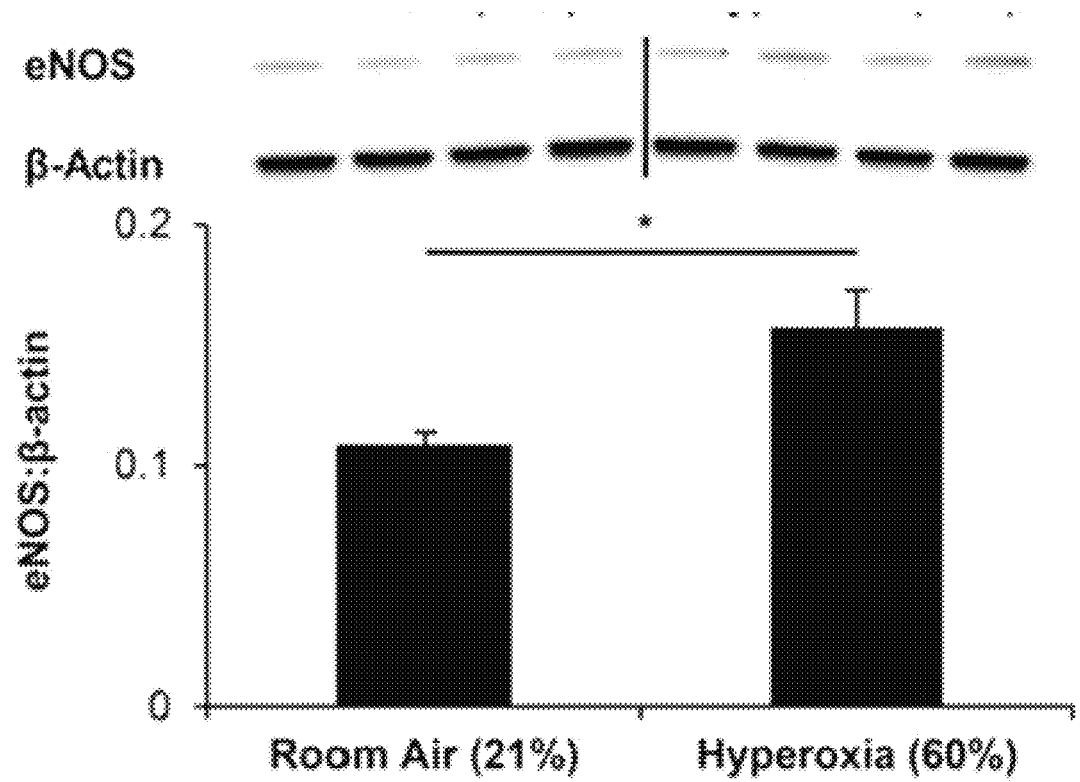
Figure 3:
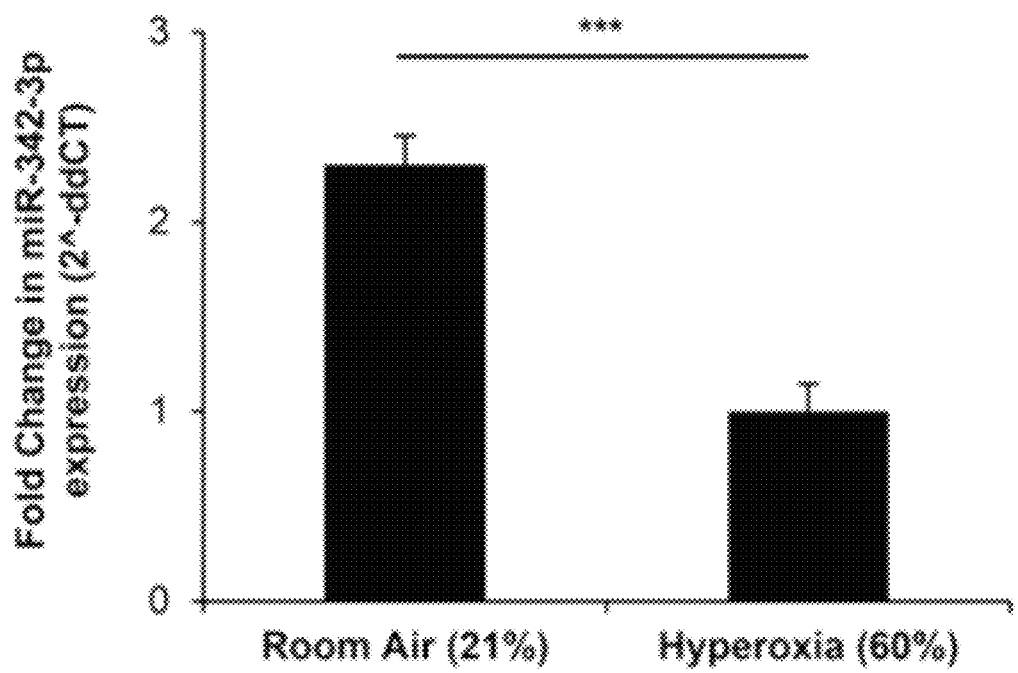
FIG. 3 illustrates a graph showing microRNA-342-3p expression in lung homogenates from 3-week-old mouse pups. Fold decreases in miR-342-3p expression were observed in hyperoxia compared with room air controls. Data were normally distributed with equal variance, so a two-tailed Student t test was used. n=6. ***P, 0.001.
Figure 4:
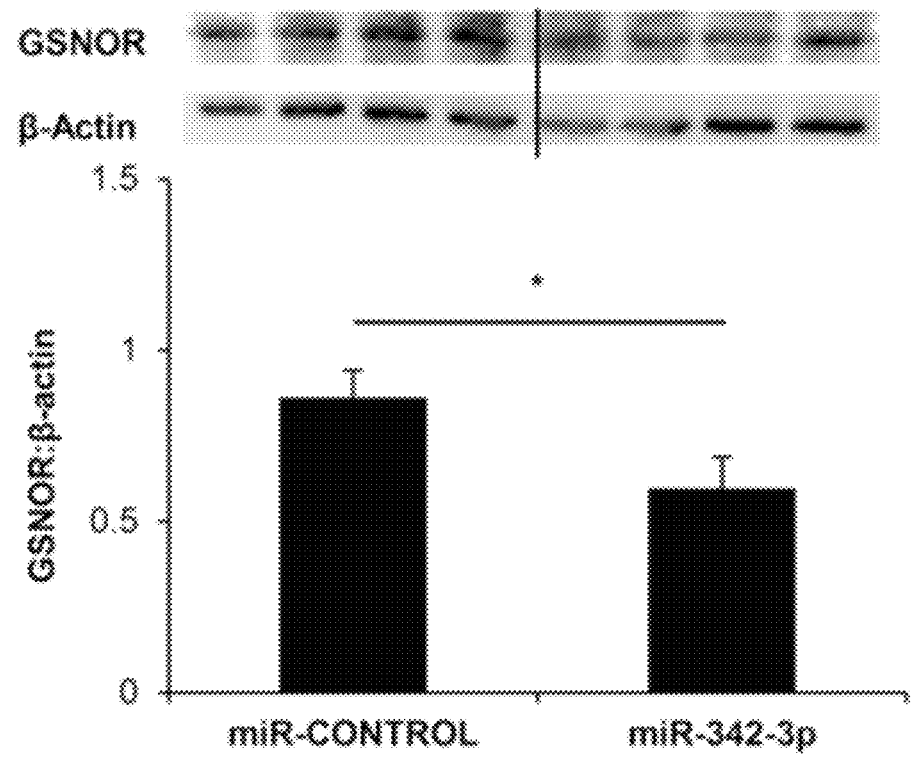
FIG. 4 illustrates a western blot and graph showing the results of miR silencing of GSNOR protein expression in mouse macrophage RAW264.7 cells were transiently transfected with a miR-342-3p mimic or a miR mimic control (cel-miR-67). Western blot analysis for GSNOR was performed on lysed cells 48 hours after transfection. Representative Western blot bands from the same gel are shown. Relative expression of GSNOR:b-actin ratio was decreased in cells overexpressing miR-342-3p. Data were normally distributed with equal variance, so a two-tailed Student t test was used. n=8. *P, 0.05.
Figure 5A:
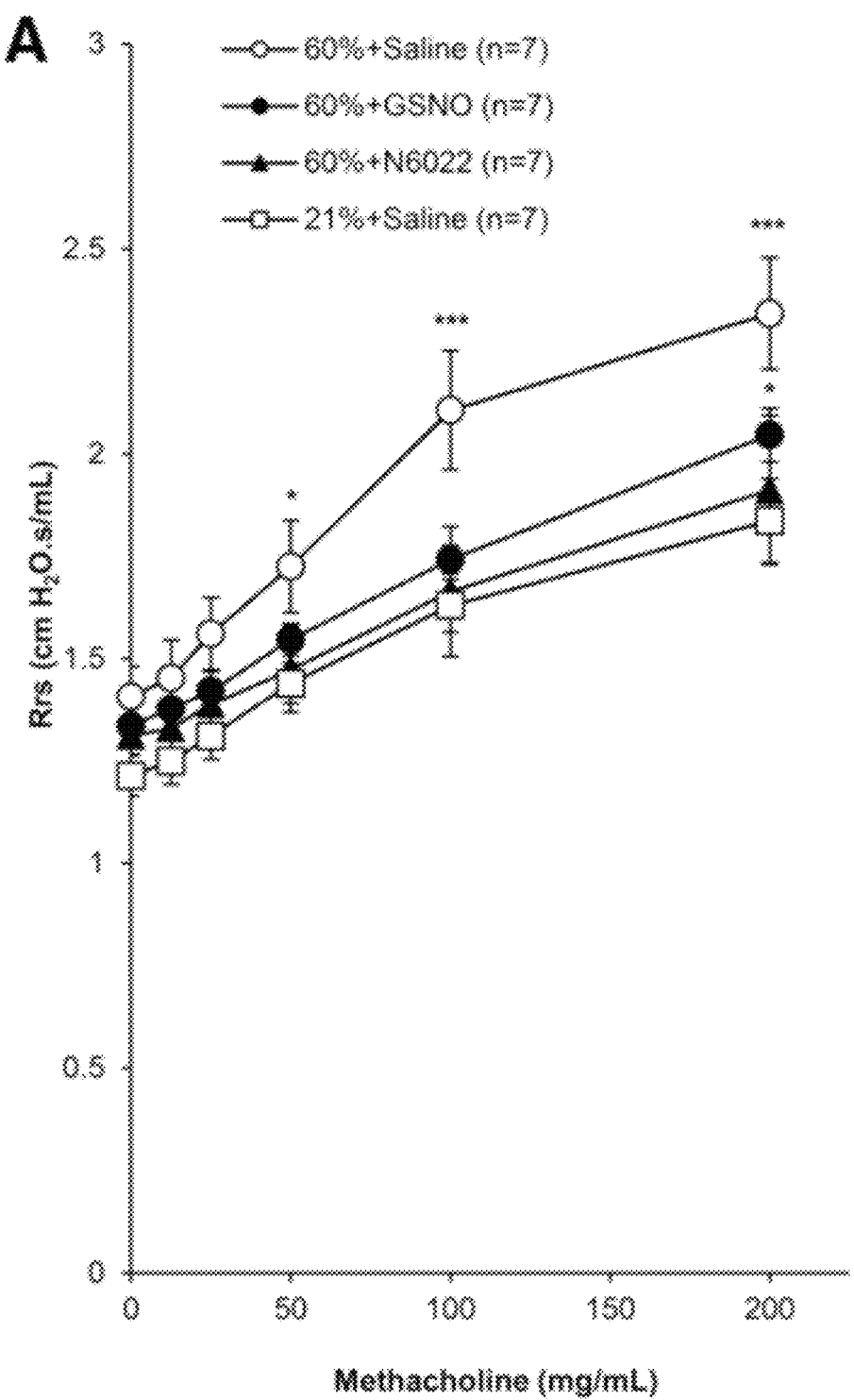
FIGS. 5(A-B) illustrate plots showing GSNO aerosol or GSNOR inhibition attenuates hyperoxia-induced airway hyperresponsiveness to methacholine challenge. Aerosolized methacholine dose responses were compared in (A) 3-week-old mouse pups raised from birth in room air (21%) or hyperoxia (60%) and in (B) adult 6-week-old mice raised in room air or recovered in room air after the initial 3-week hyperoxia exposure. Mice were pretreated with saline vehicle aerosol, 10 mM GSNO aerosol, or 1 mg/kg N6022 GSNOR inhibitor injection. Rrs was significantly increased in hyperoxia at 3 weeks and after room air recovery at 6 weeks of age; pretreatment with GSNO or N6022 attenuated these changes. Comparisons were made to 21%+saline control. Two-way analysis of variance with fixed sequence Tukey-Kramer post hoc analysis from highest to lowest methacholine dose was used. *P, 0.05, P, 0.01, *P, 0.001.
Figure 5B:
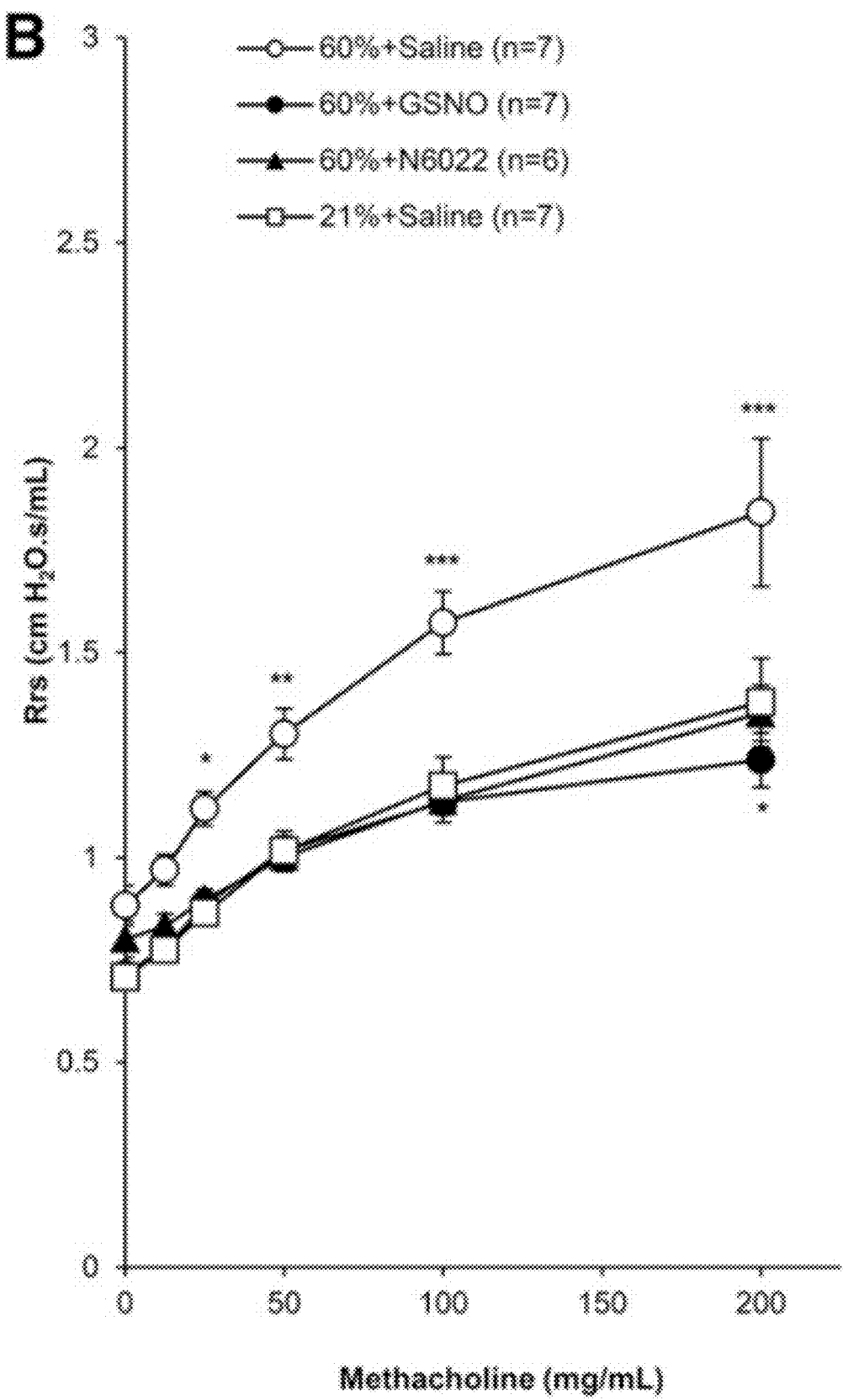

The relative protein expression of eNOS was increased in the lungs of 3-week-old mice raised in hyperoxia when compared with room air controls, as assessed by Western blot (FIG. 1D). iNOS expression was not significantly different between groups, and neuronal NOS was not detected in the lungs of either group by this Western blot preparation (data not shown).

GSNOR Gene Expression is not Increased after Neonatal Hyperoxia

To determine whether differences in GSNOR expression were transcriptionally mediated, we performed qRT-PCR on lung homogenates from 3-week-old mice raised in hyperoxia or room air. GSNOR mRNA expression did not differ between groups.

GSNOR Immunohistochemistry

GSNOR immunostaining was prominent in the hyperoxia-exposed 3-week-old mice and, consistent with previous findings, staining was localized to the epithelium and smooth muscle of the airways (FIG. 2).

Mmu-miR-342-3p Gene Expression is Decreased after Neonatal Hyperoxia

Because GSNOR mRNA expression did not explain differences in GSNOR protein expression, we next investigated whether microRNA gene silencing regulates its expression. Microarray analysis performed on lung homogenates from individual 3-week-old animals identified miR candidates found to have decreased expression in hyperoxia. MicroRNA candidates were then cross-referenced with the highest predicted gene-miR interactions to adh5, the GSNOR gene. mmu-miR-342-3p showed trends toward decreased expression in hyperoxia by microarray and was predicted by six different prediction data sets to interact with the 39 untranslated region of GSNOR. mmu-miR-342-3p was confirmed by qRT-PCR to be significantly underexpressed in the lungs of hyperoxia exposed 3-week-old mice when compared with room air controls (FIG. 3).

Transfection with miR-342-3p Decreases GSNOR Expression

We next showed that miR-342-3p decreases protein expression of GSNOR using mouse macrophage RAW 264.7 cells. RAW 264.7 cells endogenously express GSNOR (confirmed by Western blot in naive cells and those activated with cytomix; no significant difference was observed with cytomix treatment) and were one of the original cell lines used to isolate and describe GSNOR (Liu et al., 2001). RAW 264.7 cells transiently transfected with a miR-342-3p mimic had decreased GSNOR protein expression compared with cells transfected with a miR mimic control (FIG. 4). We confirmed miR-342-3p overexpression following transfection by qRT-PCR.

Hyperoxic Changes in Respiratory Mechanics are Attenuated by Pretreatment with a GSNO Aerosol or by GSNOR Inhibition We have shown that neonatal hyperoxia increased GSNOR activity and expression.

Therefore, we tested whether GSNO repletion or GSNOR inhibition could reverse the airway hyperreactivity observed in our BPD model. Responses to methacholine-provoked airway hyperresponsiveness were characterized by measuring Rrs, an indicator of airway hyperreactivity. Compared with room air controls, 3-week-old mice raised in hyperoxia displayed elevated Rrs in response to aerosolized methacholine challenge (FIG. 5A). Pretreatment of the hyperoxia-exposed mice with a 10-second GSNO aerosol attenuated these changes, such that this group was no longer significantly different from room air controls, except at the highest methacholine dose (200 mg/mL). Pretreatment of the hyperoxia-exposed mice with an i.p. injection of a selective inhibitor of GSNOR activity, N6022, attenuated these changes as well, such that this group was no longer significantly different from room air controls at all methacholine doses. Next we show in room air-recovered six-week-old animals that neonatal hyperoxia-exposed mice continued to have elevated Rrs in response to aerosolized methacholine challenge when compared with room air-raised controls (FIG. 5B). In these six-week-old mice exposed to neonatal hyperoxia, both pretreatment with GSNO aerosolization and GSNOR inhibition with N6022 remained effective in attenuating the hyperoxia induced airway hyperresponsiveness. At both ages, pretreatment with GSNO in room air-exposed mice did not significantly change Rrs when compared with room air saline-treated controls (data not shown), and baseline Rrs prior to aerosolizations was not statistically different between groups (data not shown).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating bronchopulmonary dysplasia (BDP) in a subject in need thereof, the method comprising:

administering to the subject therapeutically effective amounts of GSNO and a GSNO reductase (GSNOR) inhibiting agent, wherein the GSNOR inhibiting agent is a compound having the formula:

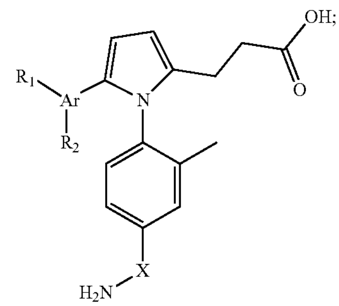

wherein Ar is an aryl;

$R_1$ is selected from the group consisting of unsubstituted or substituted imidazolyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl; and X is selected from the group consisting of CO and $SO_2$; and pharmaceutically acceptable salts thereof.

2. The method of claim 1, the subject comprising a prematurely born neonatal human subject.

3. The method of claim 1, wherein the GSNO is aerosolized GSNO.

4. The method of claim 3, the aerosolized GSNO administered to the subject at a dose of about 1 μg/kg to 10 g/kg body weight daily.

5. The method of claim 1, the compound having the formula:

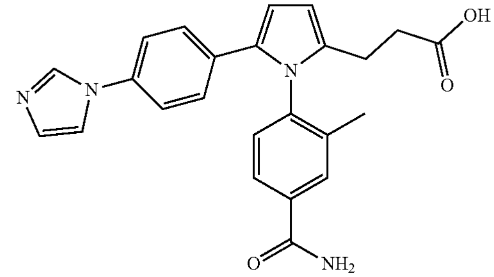 [SMILES: Cc1cc(C(N)=O)ccc1-n1c(CCC(=O)O)ccc1-c1ccc(-n2ccnc2)cc1]

and pharmaceutically acceptable salts thereof.

6. The method of claim 1, the GSNOR inhibiting agent is administered to the subject via intraperitoneal administration.

7. The method of claim 1, wherein at least one of the GSNO or GSNOR inhibiting agent is administered to a premature subject prior to supplemental oxygen treatment.

8. The method of claim 1, wherein at least one of the GSNO or GSNOR inhibiting agent is administered to a premature subject during supplemental oxygen treatment.

9. The method of claim 1, wherein the therapeutically effective amount of GSNO and GSNOR inhibiting agent is the amount effective to increase the level of GSNO in the subject's lung tissue.

10. The method of claim 1, wherein the subject is a prematurely born neonatal human exposed to supplemental oxygen treatment and at least one of the GSNO or GSNOR inhibiting agent is administered prior to supplemental oxygen treatment.

11. The method of claim 1, wherein the subject is a prematurely born neonatal human exposed to supplemental oxygen treatment and at least one of the GSNO or GSNOR inhibiting agent is administered during supplemental oxygen treatment.

* * * * *